United States Patent
M R et al.

(10) Patent No.: US 10,055,971 B2
(45) Date of Patent: Aug. 21, 2018

(54) SAFETY COMMUNICATOR—CONVERGENCE OF BODY VITALS AND TOXIC GAS PARAMETERS INTO SMARTPHONE APP TO ENHANCE SAFETY MONITORING

(71) Applicant: Honeywell International Inc., Morris Plains, NJ (US)

(72) Inventors: Gowrishankar M R, Bangalore (IN); Anand Tyagaraj, Bangalore (IN); Peter Hsi, Dublin, CA (US); Shashikant Gulaguli, Bangalore (IN); James Liu, Livermore, CA (US); Patrick Gonia, Maplewood, MN (US); Saurabh Shah, Fremont, CA (US); Praveen Sharma, Dublin, CA (US); Tarun Kumar, Irving, TX (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/532,626

(22) PCT Filed: Nov. 27, 2015

(86) PCT No.: PCT/US2015/062823
§ 371 (c)(1),
(2) Date: Jun. 2, 2017

(87) PCT Pub. No.: WO2016/089708
PCT Pub. Date: Jun. 9, 2016

(65) Prior Publication Data
US 2017/0330444 A1 Nov. 16, 2017

Related U.S. Application Data

(60) Provisional application No. 62/113,993, filed on Feb. 9, 2015.

(30) Foreign Application Priority Data

Dec. 3, 2014 (IN) .......................... 6096/CHE/2014
Mar. 9, 2015 (IN) .......................... 1149/CHE/2015

(51) Int. Cl.
*G08B 25/01* (2006.01)
*G08B 21/18* (2006.01)
(Continued)

(52) U.S. Cl.
CPC .......... *G08B 25/016* (2013.01); *G08B 21/12* (2013.01); *G08B 21/182* (2013.01); *G08B 25/10* (2013.01);
(Continued)

(58) Field of Classification Search
CPC ................................................. G06F 19/3418
See application file for complete search history.

(56) References Cited

U.S. PATENT DOCUMENTS

| 5,568,121 A | 10/1996 | Lamensdorf |
| 2006/0252999 A1 | 11/2006 | Devaul et al. |

(Continued)

FOREIGN PATENT DOCUMENTS

| CN | 107004057 | 8/2017 |
| EP | 3227808 | 10/2017 |

(Continued)

OTHER PUBLICATIONS

International Application No. PCT/US2015/062823, International Search Report dated Feb. 17, 2016, 3 pages.
(Continued)

*Primary Examiner* — Laura Nguyen
(74) *Attorney, Agent, or Firm* — Wick Phillips Gould & Martin, LLP

(57) ABSTRACT

Embodiments relate generally to systems and methods for communication between one or more personal protection
(Continued)

equipment (PPE) devices, a mobile device, and a central monitoring station. Personnel may wear PPE devices for detection and communication. These portable devices may communicate wirelessly, over a wireless fidelity (Wi-Fi) network, via Bluetooth, or another wireless connection. Systems may include a smartphone application operable to receive and combine information from each of the PPE devices. The application may also display the information to the user. In some embodiments, the application may transfer the data to a cloud storage network via a cellular network. Additionally, the application may communicate the combined data from all of the PPE devices to the central monitoring station.

19 Claims, 3 Drawing Sheets

(51) Int. Cl.
  G08B 21/12 (2006.01)
  G08B 25/10 (2006.01)
  G06F 19/00 (2018.01)
  G06Q 50/26 (2012.01)
  G16H 40/63 (2018.01)

(52) U.S. Cl.
  CPC ....... *G06F 19/3406* (2013.01); *G06Q 50/265* (2013.01); *G16H 40/63* (2018.01)

(56) References Cited

U.S. PATENT DOCUMENTS

| | | | |
|---|---|---|---|
| 2007/0005267 A1 | 1/2007 | Li | |
| 2011/0161885 A1 | 6/2011 | Gonia et al. | |
| 2013/0013331 A1* | 1/2013 | Horseman | G06F 19/3418 705/2 |
| 2016/0014249 A1* | 1/2016 | Ghazarian | H04M 1/6066 455/569.1 |
| 2007/0100213 A1 | 4/2017 | Kuo | |
| 2018/0000651 A1* | 1/2018 | Pan | A61F 13/06 |
| 2018/0075222 A1* | 3/2018 | Chen | G16H 10/40 |

FOREIGN PATENT DOCUMENTS

| | | |
|---|---|---|
| WO | 2013006644 A2 | 1/2013 |
| WO | 2016089708 A1 | 6/2016 |

OTHER PUBLICATIONS

International Application No. PCT/US2015/062823, Written Opinion of the International Searching Authority dated Feb. 17, 2016, 6 pages.
Anonymous: "Cloud-based networking—Wikipedia, the free encyclodpedia", Feb. 4, 2014, XPO55248622, Retrieved from the Internet: URL:https://en.wikipedia.org/w/index.php?title=Cloud-based_networking&oldid=593903572, retrieved on Feb. 9, 2016, p. 1-p. 2.
Bai et al., "A Portable Oxygen Concentration Detection and Monitor System Using a Smartphone and a Portable Sesnor Module", Consumer Electronics, Taiwan, (ICCE-TW), 2-14 IEEE International Conference on Consumer Electronics, May 26-28, pp. 129-130.
Anonymous: "Cloud-based networking—Wikipedia, the free encyclopedia", Feb. 4, 2014, XPO55248622, Retrieved from the Internet: URL:https://en.wikipedia.org/w/index.php?title=Cloud-based_networking&oldid=593903572, retrieved on Feb. 9, 2016, p. 1-p. 2.
International Application No. PCT/US2015/062823, International Preliminary Report on Patentability dated Jun. 15, 2017, 8 pages.
Europe Patent Application No. 15813964.2 Communication Pursuant to Rules 161(1) and 162 EPC, dated Jul. 11, 2017, 2 pages.
University at Buffalo, "First-responder location tracking/ vital monitoring system: software systems and user interface," Group 46, CSE 442, Oct. 22, 2014, pp. 1-7.
Versel, Neil "Army-funded home telehealth system measures firefighter stress," [online], Nov. 12, 2012 [retrieved on Oct. 16, 2017]. Retrieved from the Internet: <URL: http://www.mobihealthnews.com/19031/army-funded-home- telehealth-system-measures-firefighter-stress>, pp. 1-2.

\* cited by examiner

SAFETY COMMUNICATOR—CONVERGENCE OF BODY VITALS AND TOXIC GAS PARAMETERS INTO SMARTPHONE APP TO ENHANCE SAFETY MONITORING

CROSS-REFERENCE TO RELATED APPLICATIONS

The present application is the national stage application of and claims priority to International Application Serial No. PCT/US2015/062823 filed Nov. 27, 2015 and entitled "Safety Communicator—Convergence of Body Vitals and Toxic Gas Parameters into Smartphone App to Enhance Safety Monitoring," which claims priority to India Provisional Patent Application No. 6096/CHE/2014 filed Dec. 3, 2014 by Gowrishankar M R et al., and entitled "Safety Communicator—Convergence of Body Vitals and Toxic Gas Parameters into Smartphone App to Enhance Safety Monitoring,"; U.S. Provisional Application Ser. No. 62/113,993 filed Feb. 9, 2015 by Gowrishankar M R et al., and entitled "Safety Communicator—Convergence of Body Vitals and Toxic Gas Parameters into Smartphone App to Enhance Safety Monitoring"; and India Provisional Patent Application No. 1149/CHE/2015 filed Mar. 9, 2015 by Gowrishankar M R et al., and entitled "Safety Communicator—Convergence of Body Vitals and Toxic Gas Parameters into Smartphone App to Enhance Safety Monitoring," all of which are incorporated herein by reference as if reproduced in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

While working in a facility where there may be a hazardous environment, a user may wear a number of personal protection equipment (PPE) devices operable to protect the user from the hazardous environment. These PPE devices may provide protection and may possibly monitor the environment and the user's exposure to the environment to further ensure the protection of the user. Various PPE devices may be enabled to communicate over wireless communication channels.

SUMMARY

Aspects of the disclosure may include embodiments of a method of combining data from multiple personal protection equipment (PPE) devices and communicating the data, wherein the method is completed by an application executed on a mobile device, the method comprising receiving, by the application, data read by one or more PPE device, using wireless communication channels; evaluating, by the application, the data readings sent by the PPE device(s); determining if the data readings are within a present limit; when the data readings are within a preset limit, displaying the data on a user interface (UI); transmitting the data to a central monitoring station; sending the data to a cloud network; when the data readings are above or below the preset limit, reading out an alarm status, by the application; alerting the user, via the UI, of the alarm status; and sending the data to the cloud network.

In some embodiments, the method may further comprise analyzing the data, by the cloud network; saving the analyzed data in the cloud for future reference, such as for maintenance or audits; and sending the data to the central monitoring station. In some embodiments, the data is read and received at preconfigured time intervals. In some embodiments, the data is read and received continually. In some embodiments, the method may further comprise sending a message to one or more preconfigured identifier. In some embodiments, the method may further comprise communicating data to a second user interface worn by the user. In some embodiments, the method may further comprise communicating data from an audio message to a headset worn by the user. In some embodiments, the method may further comprise communicating with a user identifier (ID); receiving user identification data from the user ID; and associating PPE data received by the mobile device with the user identification data. In some embodiments, the mobile device facilitates all communication between the PPE devices and the central monitoring station.

Additional aspects of the disclosure may include embodiments of an application executed by a mobile device operable to receive data from one or more PPE devices, wherein the PPE devices communicate wirelessly with the mobile device; evaluate the data received from the PPE devices; display the data received from the PPE devices on a user interface of the mobile device; when an alarm status is detected from one or more of the PPE devices, displaying an alarm status on the user interface of the mobile device; forward the data received from the PPE devices to a central monitoring station; and forward the data received from the PPE devices to a cloud network.

In some embodiments, the application may be further operable to communicate data to a second user interface worn by the user. In some embodiments, the application may be further operable to communicate an audio message to a headset worn by the user. In some embodiments, the application may be further operable to communicate with a user identifier (ID); receive user identification data from the user ID; and associate PPE data received by the mobile device with the user identification data. In some embodiments, the PPE devices communicating with the application comprise one or more of the following: fall protection systems, gas detectors, respiratory protection, a bio harness, hearing protection, electrical safety equipment, first responder equipment, eye, face, and head protection, body protection, and footwear. In some embodiments, the data received from the PPE devices comprises one or more of the following: fall detection and alert, personal airbag, predictive fall prevention, man down alarms or alerts, gas level readings, gas identification, exposure data, gas detector alarms or alerts, exposure count, environmental hazards, breath analysis, drug and alcohol detection, and respiratory alarms or alerts, vital parameters, heart rate, electromagnetic pulse (EMP), temperature, respiratory rate, active noise cancelling information, in-ear dosimetry, hearing protection alarms or alerts, voltage detection, wireless meters, energy harvesting, digital work permit information, physiological monitoring and tracking, hand free navigation, incident management, air quality information, heads up display information, workflow navigation, hands-free work, voice control, impact sensing, vital signs monitoring, stress and comfort, replacement notification, compliance monitoring, asset tracking, sip hazards, liquid detection, fatigue monitoring, location services, and step and/or wear counts.

Other aspects of the disclosure may include embodiments of a mobile device comprising a user interface; a plurality of wireless communication elements; a processor; a memory; an application stored in the memory and executed by the processor to receive data from one or more PPE devices, wherein the PPE devices communicate wirelessly with the mobile device; evaluate the data received from the PPE devices; display the data received from the PPE devices on a user interface of the mobile device; when an alarm status is detected from one or more of the PPE devices, displaying an alarm status on the user interface of the mobile device; forward the data received from the PPE devices to a central monitoring station; and forward the data received from the PPE devices to a cloud network.

In some embodiments, the mobile device facilitates all communication between the PPE devices and the central monitoring station. In some embodiments, the application may be further operable to send a notification to one or more of the PPE devices when the mobile device is not communicating with the central monitoring station, wherein the PPE device activates communication between the PPE device and the central monitoring station. In some embodiments, the plurality of wireless communication elements comprises one or more of the following: Wi-Fi, Bluetooth, near-field communication (NFC), radio frequency identification (RFID), radio, and cellular. In some embodiments, the application is further operable to combine at least a portion of the received data to generate a health status for the user.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
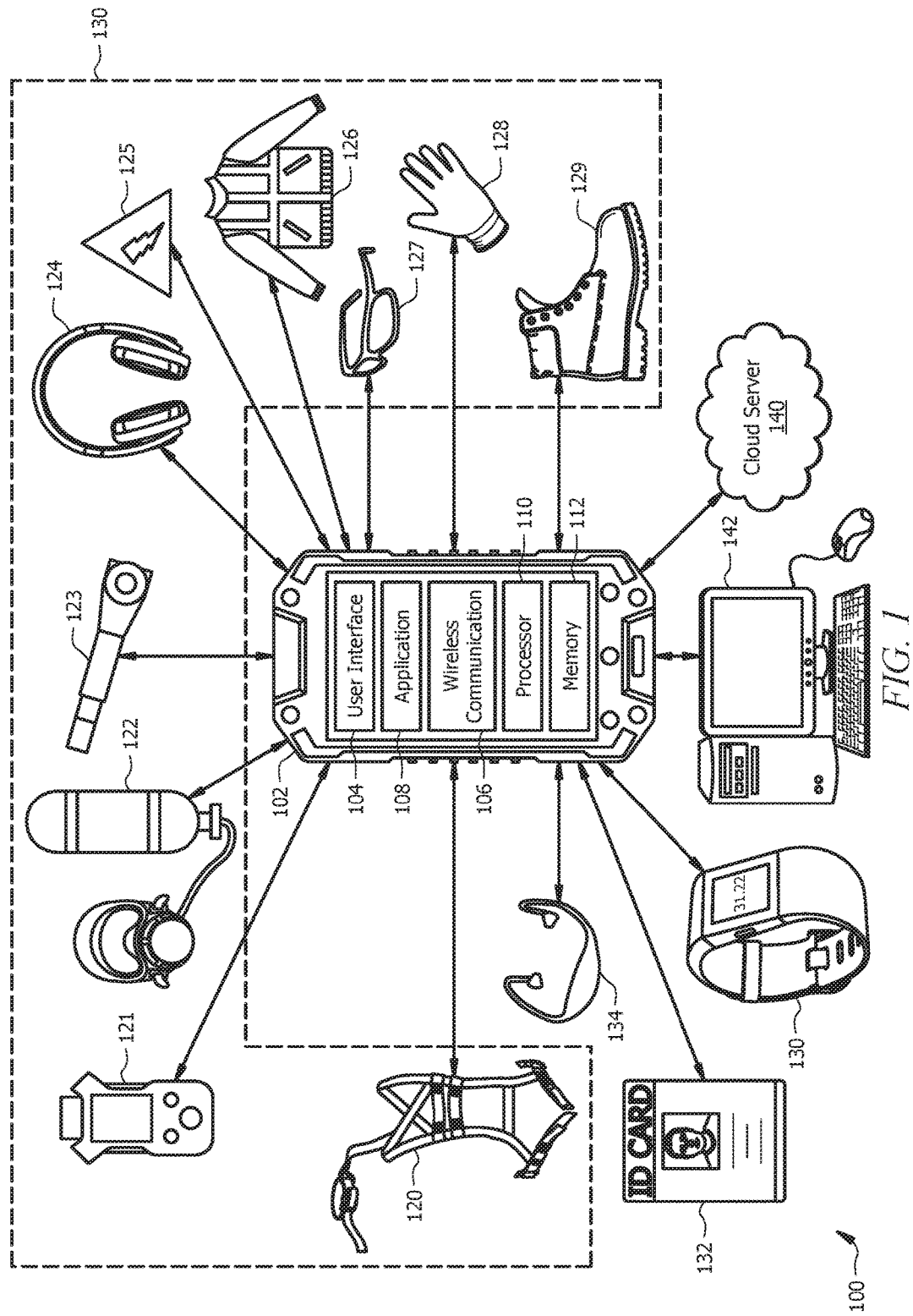
FIG. 1 illustrates a communication system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure relate to communication solutions for monitoring personnel working in areas where toxic gas may be in the environment. Personnel may wear one or more personal protection equipment (PPE) devices for detection and communication. For example, a person may wear a portable gas detector operable to identify gases in the air and determine the levels of gases in the environment. Also, a person may wear any number of monitoring devices that may monitor movement, breathing, heart rate, etc. Additionally, personnel may wear portable location devices operable to communicate the location of the device (and therefore the user) to a central monitoring station. These portable devices may communicate wirelessly, over a wireless fidelity (Wi-Fi) network, via Bluetooth, or another wireless connection.

In some embodiments, PPE devices may have alarms, notifications, or updates that are communicated to the user via sounds, vibrations, and/or visual notifications. If a user is employing multiple PPE devices the alerts and warnings from each of the devices may vary, making it difficult for the user to interact with and respond to the PPE devices. This may cause delays in action when an emergency occurs. Also, each PPE device may communicate individually with the central monitoring station, employing multiple wireless infrastructures or communication channels. Additionally, there may be no communication between the PPE devices. Some PPE devices may also be difficult to operate wearing protective gloves.

Applicants have developed systems and methods for addressing these issues. Systems may include a smartphone application (which may be called a Safety Communicator application) operable to receive and combine information from each of the PPE devices. For example, the application may establish a connection between the smartphone and each of the PPE devices, which may be wireless connections, such as Wi-Fi or Bluetooth. The application may then receive data from each of the PPE devices, and store the data locally on the device. The application may also display the information to the user. In some embodiments, the application may transfer the data to a cloud storage network via a cellular network. Additionally, the application may communicate the combined data from all of the PPE devices to the central monitoring station.

The application may automatically receive data from the PPE devices and send the data to the central monitoring station, so that in an emergency situation, the user would not be responsible for the communication. Additionally, the application may be operable to send messages or calls to other mobile devices if needed, such as in an alarm or emergency situation.

The application may present or display information to the user via a user interface on the smartphone or connected to the smartphone (such as a smartwatch). The application may compile the information received from each of the PPE devices into a consistent format, making it easier to read and understand. The user may be able to input commands to the application, such as adjusting alarm limits and settings in the application, which may then be communicated from the smartphone to the PPE device(s). The application may show real-time readings via the user interface, and may issue alerts or warnings via the user interface. Additionally, vibrations or audible alerts may also be issued by the application via the smartphone. In some cases, the application may be operable to communicate with a headset or earpiece (such as a Bluetooth headset for example) worn by the user to communicate audible alerts or warnings.

Combining the data from a plurality of PPE devices into one application may simplify the interaction for a user, may make the data available to more users via the cloud network, and may provide improved safety for the user by issuing automated alerts and warnings, as well as sending messages and/or voice calls to other devices and/or the central monitoring station.

Referring to FIG. 1, a system 100 is illustrated, wherein the system 100 may comprise a mobile device 102. The mobile device 102 may comprise a smartphone, tablet, or other handheld device. The mobile device 102 may comprise a user interface 104 operable to communicate information to a user and receive input from a user. The mobile device 102 may comprise wireless communication elements 106, and may be operable to wirelessly communicate with a plurality of devices. In some embodiments, the mobile device 102 may be operable to communicate via Wi-Fi, Bluetooth, NFC, RFID, radio, cellular, or any other wireless communication system.

In some embodiments, the mobile device 102 may communicate with a plurality of PPE devices (such as a smart watch) 130. These PPE devices 130 may include fall protection systems 120, gas detectors 121, respiratory protection 122, a bio harness 123, hearing protection 124, electrical safety equipment 125, first responder equipment 126, eye, face, and head protection 127, body protection 128 (such as gloves), and footwear 129. The PPE devices 130 shown in FIG. 1 are examples of devices that may be worn by the user and communicate with the mobile device 102, but other PPE devices 130 may be capable of communicating with the mobile device 102 via wireless communication, as well.

Fall protection systems 120 may communicate data to the mobile device 102, such as fall detection and alert, personal airbag, predictive fall prevention, and man down alarms or alerts. Gas detectors 121 may communicate data to the mobile device 102, such as gas level readings, gas identification, exposure data, and any alarms or alerts. Respiratory protection 122 may communicate data to the mobile device 102, such as exposure count, environmental hazards, breath analysis, drug and alcohol detection, and any alarms or alerts.

The bio harness 123 may read a wearer's vital parameters, such as heart rate, electromagnetic pulse (EMP), temperature, respiratory rate, etc. The bio harness 123 may be operable to communicate the wearer's vital parameters to the mobile device 102. Hearing protection 124 may include active hearing protection and/or passive hearing protection, ear buds, ear muffs, and other hearing protection devices. The hearing protection 124 may communicate data to the mobile device 102, such as virtual training, process verification, active noise cancelling information, in-ear dosimetry, and any alarms or alerts.

Electrical safety equipment 125 may communicate data to the mobile device 102, such as voltage detection, wireless meters, energy harvesting, and digital work permit information. First responder equipment 126 may communicate data to the mobile device 102, such as physiological monitoring and tracking, hand free navigation, incident management, and air quality information. In some embodiments, first responder equipment may include other PPE devices, such as gas detectors, bio harnesses, location devices, etc.

Eye, face, and head protection 127 may include glasses, goggles, helmets, face shields, face masks, among other devices. Eye, face, and head protection 127 may communicate data to the mobile device 102, such as heads up display information, workflow navigation, hands-free work, voice control, and impact sensing. Gloves 128 and other body protection may include protective clothing, hoods, suits, gloves, sleeves, aprons, among other body protection. Body protection 128 may communicate data to the mobile device 102, such as vital signs monitoring, stress and comfort, replacement notification, compliance monitoring, and asset tracking. In some embodiments, the bio harness 123 may be incorporated into body protection 128. Footwear 129 may communicate data to the mobile device 102, such as sip hazards, liquid detection, fatigue monitoring, location services, and step and/or wear counts.

The mobile device 102 may receive data, as described above, from any number of PPE devices 130. The mobile device 102 may comprise an application 108 operable to receive, process, and compile the data into an easy-to-read format. The mobile device 102 may also comprise a processor 110 and a memory 112, wherein the application 108 is stored in the memory 112 and executed by the processor 110. The application 108 may display the data via the user interface 104 of the mobile device 102. In some embodiments, some of the information may be combined to simplify the display, and may be combined to generate a health status for the user.

In some embodiments, the mobile device may also communicate with other devices, such as a user identifier (ID) 132, a smart watch 130, and a Bluetooth headset 134. The user ID 132 may communicate user identification information to the mobile device 102. In some embodiments, the application 108 may be operable to associate data received from the PPE devices (130) by the mobile device 102 with the user identification information (or data). The smart watch 130 may act as a second user interface for the mobile device 102, and may display information from the application 108 of the mobile device 102, and may also receive input from the user that is communicated to the mobile device. Additionally, a user may wear a Bluetooth or wireless headset 134, wherein the application 108 of the mobile device 102 may send information to the user via the headset 134, such as an audio message or alert.

In some embodiments, the mobile device 102 may store the data received from the PPE (and other) devices. The mobile device 102 may also communicate the data to a cloud server (or storage, or network) 140, wherein the data may be accessed by other systems for monitoring purposes. In some embodiments, a plurality of mobile devices carried by a plurality of users may communicate data to the cloud server 140. Different management systems may analyze the data to generate monitoring reports for a group of users. In some embodiments, the mobile device 102 may communicate with a central monitoring station 142, wherein the mobile device 102 may send data to the central monitoring station 142. In some embodiments, the central monitoring station 142 may receive data from the mobile device 102 via the cloud server 140.

In some embodiments, the cloud server 140 may provide access to a public network for the data received by the mobile device 102, while the PPE devices 130, other devices, and central monitoring station 142 may communicate via a private or enterprise network. In some embodiments, the mobile device 102 may be operable to communicate with other mobile devices. For example, in the event of an alarm, the mobile device 102 may be operable to send a message to one or more preconfigured identifier, such as a mobile number and/or email address.

In some embodiments, the mobile device 102 may handle (or facilitate) all communication between the PPE devices 130 and the cloud server 140 and central monitoring station 142. In other words, the PPE devices 130 may not directly communicate with the central monitoring station 142 and/or cloud server 140. Combining all of the communication from all of the PPE devices into one communication channel between the mobile device 102 and the central monitoring station 142, or between the mobile device 102 and the cloud server 140, may serve to clear up wireless communication channels that may be used if all of the PPE devices 130 individually communicated with either the central monitoring station 142 or the cloud server 140.

In other embodiments, one or more of the PPE devices (130) may be enabled to communicate with the central monitoring station 142, for example if communication is lost between the mobile device 102 and the central monitoring station 142. This may occur if the mobile device 102 loses battery life, is damaged, or otherwise unable to communicate with the central monitoring station 142. Therefore, a PPE device may receive a notification that the mobile device 102 is not communicating with the central monitoring station 142, and may activate communication between the PPE device and central monitoring station 142.

In some embodiments, the application 108 may be a sub-system of a Personal Safety Ecosystem (PSE) on the mobile device 102. The PSE may comprise multiple application or device managers on the mobile device 102.

Figure 2:
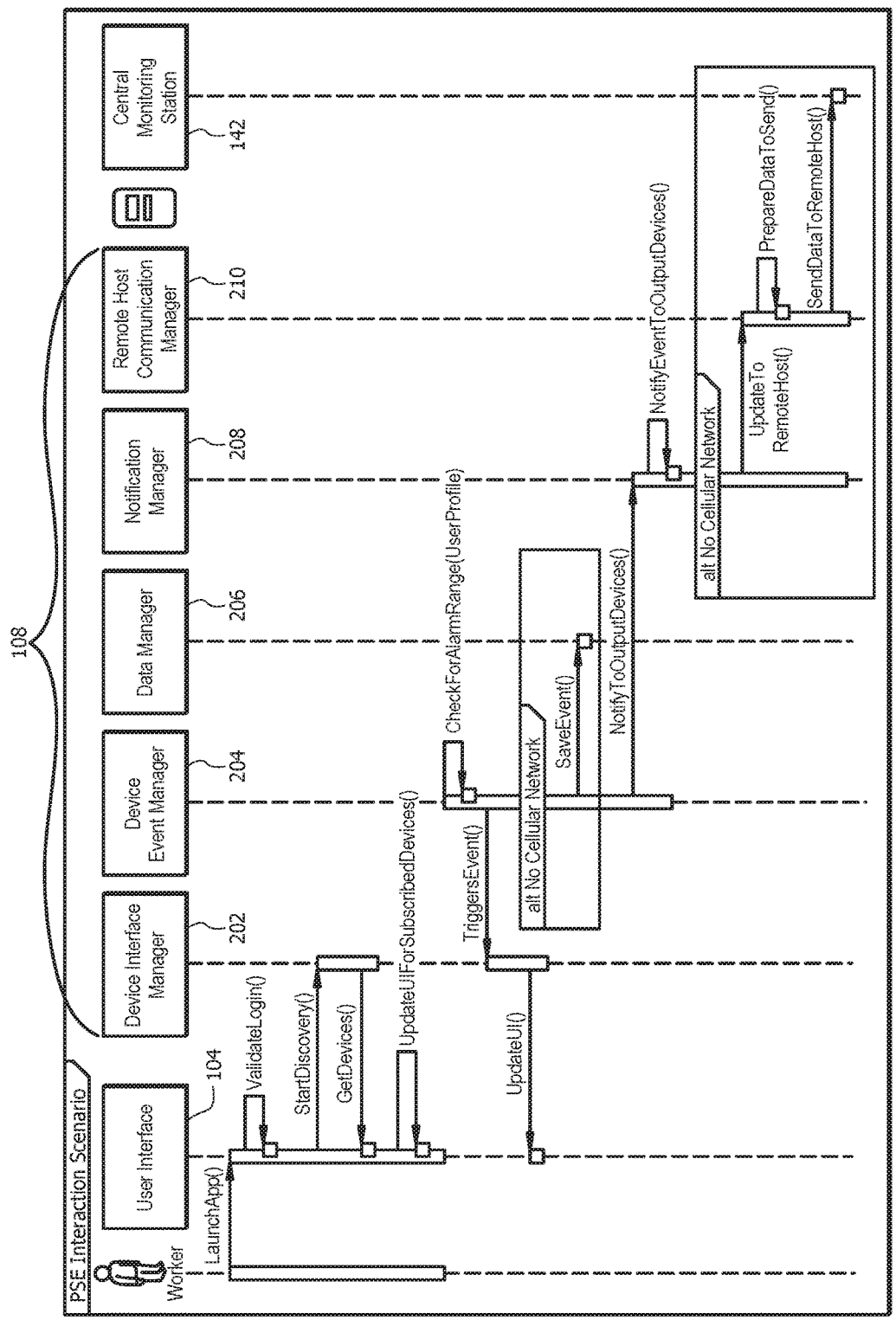
FIG. 2 illustrates a communication scenario according to an embodiment of the disclosure.

Referring to FIG. 2, a communication map is shown illustrating an interaction scenario for the PSE. A worker may launch the application 108 by interacting with the user interface (UI) 104. The application 108 may comprise a plurality of manager elements, such as a device interface manager 202, a device event manager 204, a data manager 206, a notification manager 208, and a remote host communication manager 210. The UI 104 may communicate with the device interface manager 202 to validate a login for the user, start discovery for the PPE device, and pairing with the discovered the PPE devices. Additionally, the device interface manager 202 may send an update to the UI 104 for the subscribed or paired devices, wherein the UI 104 may display the devices that have been added.

The device event manager 204 may periodically, or continually, check for alarms from the paired devices. If an alarm event is discovered from one of the devices, the device event manager 204 may send this information to the device interface manager 202, which may then send an update to the UI 104 containing the alarm information. In the event that the mobile device 102 (not shown) loses cellular communication with the central monitoring station 142, the device event manager 204 may locally save the information from the alarm event to the data manager 206. In some embodiments, the device event manager 204 may communicate the alarm event information to the notification manager 208, along with a command to notify output devices, prompting the notification manager to generate a notification for output devices. In some embodiments, the notification manager 208 may send an update to the remote host communication manager 210, wherein the update contains the alarm event information. The remote host communication manager 210 may then prepare and send data to the remote host, wherein the remote host may comprise the central monitoring station 142. In some embodiments, the communication between the remote host communication manager 210 and the central monitoring station 142 may occur over a cellular communication network.

Figure 3:
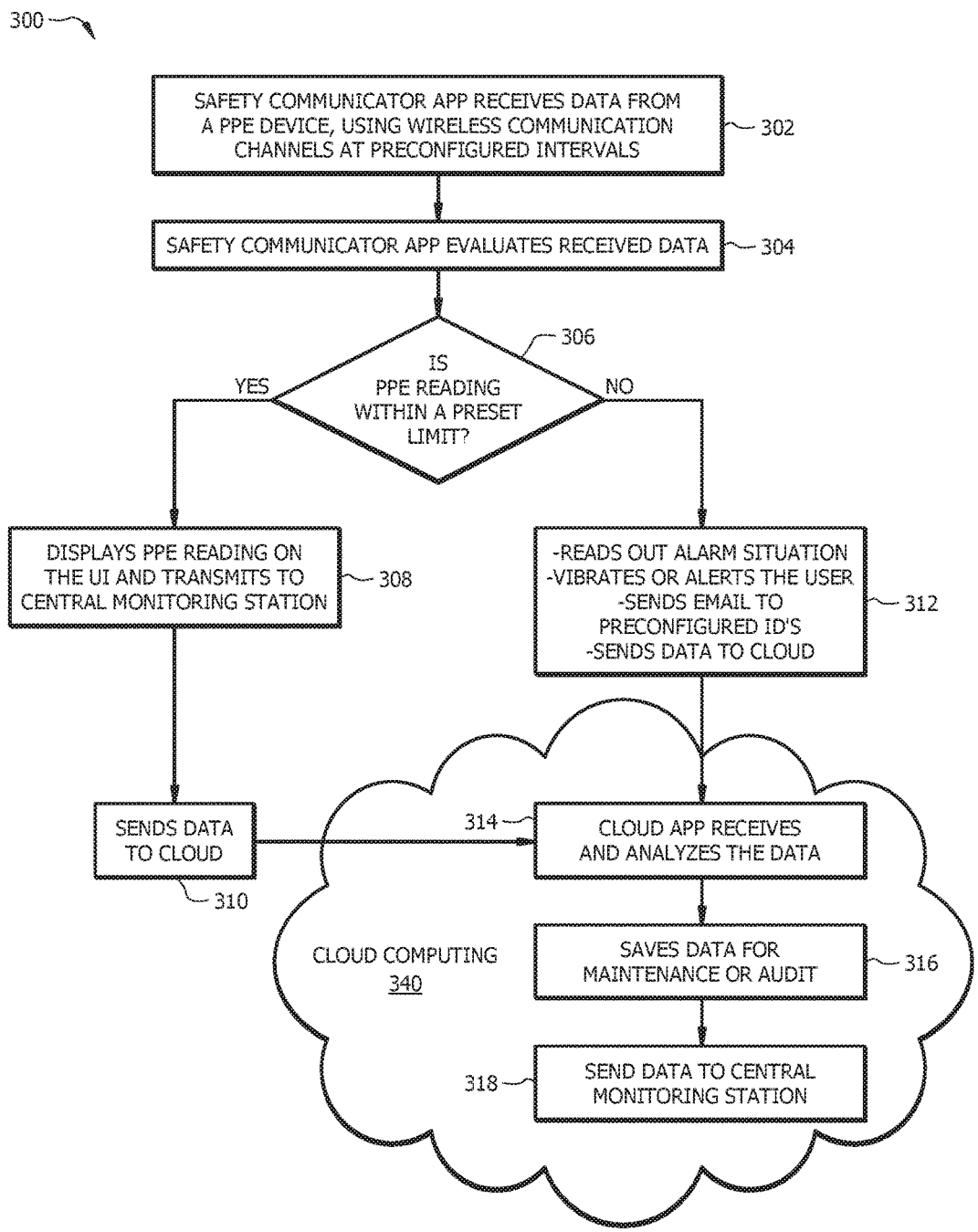
FIG. 3 illustrates a method according to an embodiment of the disclosure.

Referring now to FIG. 3, a method 300 for combining and communicating data from the PPE device to a mobile device is described. At step 302, the Safety Communicator application may receive data read by one or more PPE device(s), using wireless communication channels, wherein the data is read and received at preconfigured time intervals. In some embodiments, the data may comprise gas readings and body vitals. In other embodiments, the data may comprise any data that is listed above in FIG. 1. At step 304, the safety communicator application may evaluate the data readings sent by the PPE device(s). At step 306 it may be determined if the PPE readings are within a preset limit. When the data readings are determined to be within the preset limit at step 306, the method 300 may proceed to step 308, wherein the UI may display the data, and wherein the data may be transmitted to a central monitoring station. Additionally, at step 310 the data may be sent to the cloud 340. In some embodiments, the method may proceed to step 314. Once the data is sent to the cloud 340, at step 314, the data may be analyzed by the cloud network. At step 316, the analyzed data may be saved in the cloud for future reference, such as for maintenance or audits. At step 318, the data may be sent to the central monitoring station.

When the data readings are above or below the preset limit at step 306, the method 300 may proceed to step 312, wherein the safety communicator application may read out an alarm situation, the mobile device may vibrate or otherwise alert the user, possibly via the UI, the mobile device may send an email or other message to one or more preconfigured identifier, and the mobile device may send the data to the cloud 340. Once the data is sent to the cloud 340, at step 314, the data may be analyzed by the cloud network. At step 316, the analyzed data may be saved in the cloud for future reference, such as for maintenance or audits. At step 318, the data may be sent to the central monitoring station.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of combining data from multiple personal protection equipment (PPE) devices and communicating the data, wherein the method is completed by an application executed on a mobile device, the method comprising:

detecting, by the mobile device, one or more PPE device within a wireless communication range of the mobile device;

in response to detecting the one or more PPE device, pairing, by the mobile device, with the one or more PPE device;

receiving, by the mobile device, data read by the one or more PPE device, using wireless communication channels;

sending, by a device interface manager of the mobile device, data from the one or more PPE device to a user interface of the mobile device;

evaluating, by the mobile device, the data readings sent by the one or more PPE device;

in response to evaluating the data reading, transmitting, by the mobile device, the data to a central monitoring station;

in response to evaluating the data reading, sending, by at least one of the mobile device and the central monitoring station, the data to a cloud network;

determining that at least a portion of the data readings are within a preset limit;

in response to determining that at least a portion of the data readings are within the preset limit, displaying the data on the user interface;

determining that at least a portion of the data readings are above or below the preset limit;

in response to determining that at least a portion of the data readings are above or below the preset limit, reading out an alarm status, by the application; and in response to reading out an alarm status by the application, alerting a user, via the user interface, of the alarm status;

wherein the application is configured to send a notification to one or more of the PPE devices when the mobile device is not communicating with the central monitoring station, wherein the PPE device activates communication between the PPE device and central monitoring station.

2. The method of claim 1, wherein the method further comprises:

determining, by a device event manager of the mobile device, that an alarm event has been received from at least one PPE device;

receiving, by the device interface manager, the alarm event information; and sending, by the device interface manager, an update to the user interface containing the alarm event information.

3. The method of claim 1, wherein the method further comprises:

detecting, by the mobile device, a second PPE device within a wireless communication range of the mobile device;

in response to detecting the second PPE device, pairing, by the mobile device, with the second PPE device;

receiving, by the mobile device, data read by the second PPE device, using wireless communication channels; and sending, by the device interface manager of the mobile device, data from the second PPE device to the user interface of the mobile device.

4. The method of claim 1, wherein the data is read and received at preconfigured time intervals.

5. The method of claim 2, wherein the data is read and received continually.

6. The method of claim 1, further comprising communicating data to a second user interface worn by the user.

7. The method of claim 1, further comprising communicating data from an audio message to a headset worn by the user.

8. The method of claim 1, further comprising:
communicating with a user identifier;
receiving user identification data from the user identifier; and
associating PPE data received by the mobile device with the user identification data.

9. The method of claim 1, wherein the mobile device facilitates all communication between the PPE device(s) and the central monitoring station.

10. An application executed by a mobile device configured to:
detect one or more PPE device within a wireless communication range of the mobile device;
in response to detecting the one or more PPE device, pair with the one or more PPE device;
receive data from the one or more PPE device, wherein the one or more PPE device communicates wirelessly with the mobile device;
evaluate the data received from the one or more PPE device;
display the data received from the one or more PPE device on a user interface of the mobile device;
detect an alarm status from at least one PPE device;
in response to detecting the alarm status from at least one PPE device, displaying an alarm status on the user interface of the mobile device;
forward the data received from the one or more PPE device to a central monitoring station; and
forward the data received from the one or more PPE device to a cloud network;
wherein the application is configured to send a notification to one or more of the PPE devices when the mobile device is not communicating with the central monitoring station, wherein the PPE device activates communication between the PPE device and central monitoring station.

11. The application of claim 10, wherein the application is further configured to communicate data to a second user interface worn by a user.

12. The application of claim 10, wherein the application is further configured to communicate an audio message to a headset worn by a user.

13. The application of claim 10, wherein the application is further configured to:
communicate with a user identifier;
receive user identification data from the user identifier; and
associate PPE data received by the mobile device with the user identification data.

14. The application of claim 10, wherein the application is further configured to:
determine that an alarm event has been received from at least one PPE device;
receive the alarm event information; and
send an update to the user interface containing the alarm event information.

15. The application of claim 10, wherein the application is further configured to:
detect a second PPE device within a wireless communication range of the mobile device;
in response to detecting the second PPE device, pair with the second PPE device;
receive data read by the second PPE device, using wireless communication channels; and
display the data received from the second PPE device on the user interface of the mobile device.

16. A mobile device comprising:
a user interface;
a plurality of wireless communication elements;
a processor;
a memory;
an application stored in the memory and executed by the processor to:
detect one or more PPE device within a wireless communication range of the mobile device;
in response to detecting the one or more PPE device, pair with the one or more PPE device;
receive data from one or more PPE device, wherein the PPE device communicates wirelessly with the mobile device;
evaluate the data received from the one or more PPE device;
display the data received from the one or more PPE device on the user interface mobile device;
detect an alarm status from at least one PPE device;
in response to detecting the alarm status from at least one PPE device, displaying an alarm status on the user interface of the mobile device;
forward the data received from the one or more PPE device to a central monitoring station; and
forward the data received from the one of more PPE device to a cloud network;
wherein the application is configured to send a notification to one or more of the PPE devices when the mobile device is not communicating with the central monitoring station, wherein the PPE device activates communication between the PPE device and central monitoring station.

17. The mobile device of claim 16, wherein the mobile device facilitates all communication between the one or more PPE device and the central monitoring station.

18. The mobile device of claim 16, wherein the plurality of wireless communication elements comprises one or more of the following: Wi-Fi, Bluetooth, near-field communication (NFC), radio frequency identification (RFID), radio, and cellular.

19. The mobile device of claim 16, wherein the application is further configured to combine at least a portion of the received data to generate a health status for the user.

* * * * *

UNITED STATES PATENT AND TRADEMARK OFFICE
CERTIFICATE OF CORRECTION

PATENT NO. : 10,055,971 B2
APPLICATION NO. : 15/532626
DATED : August 21, 2018
INVENTOR(S) : Gowrishankar M R et al.

It is certified that error appears in the above-identified patent and that said Letters Patent is hereby corrected as shown below:

On the Title Page

Page 2 Column 2 Item (56), U.S. PATENT DOCUMENTS, Line 1, "4/2017 Kuo" should be "5/2007 Dossas et al"

In the Specification

Column 7/Line 31: "(130)" should be "130"

Signed and Sealed this
Fourth Day of December, 2018

Andrei Iancu
*Director of the United States Patent and Trademark Office*